United States Patent
Cox

(10) Patent No.: US 7,044,738 B2
(45) Date of Patent: May 16, 2006

(54) SYMMETRICAL RUBBER DAM HAVING A TOOTH GRIPPING ORIFICE

(76) Inventor: Duane Edward Cox, 1410 Lavista Rd. NE., Atlanta, GA (US) 30324

( * ) Notice: Subject to any disclaimer, the term of this patent is extended or adjusted under 35 U.S.C. 154(b) by 113 days.

(21) Appl. No.: 10/437,649

(22) Filed: May 13, 2003

(65) Prior Publication Data

US 2004/0229189 A1 Nov. 18, 2004

(51) Int. Cl.
*A61C 5/14* (2006.01)
(52) U.S. Cl. .................................................. 433/136
(58) Field of Classification Search ......... 433/136–138
See application file for complete search history.

(56) References Cited

U.S. PATENT DOCUMENTS

| | | | | |
|---|---|---|---|---|
| 174,942 A | * | 3/1876 | Brown | ......................... 433/136 |
| 663,507 A | * | 12/1900 | Meguiar | ..................... 433/137 |
| 702,394 A | * | 6/1902 | Beall | ........................... 433/137 |
| 2,680,908 A | | 6/1954 | Daigle | |
| 3,772,790 A | | 11/1973 | Swan-Gett et al. | |
| 3,781,994 A | | 1/1974 | Hesselgren | |
| 4,204,329 A | * | 5/1980 | Kahn | ........................ 433/136 |
| 4,600,387 A | | 7/1986 | Ross | |
| 4,828,491 A | | 5/1989 | Gray | |
| 5,931,673 A | * | 8/1999 | Bolbolan | ..................... 433/136 |
| 6,093,022 A | * | 7/2000 | Swallow | ..................... 433/136 |
| 6,648,642 B1 | * | 11/2003 | Horvath et al. | ............. 433/136 |
| 2004/0170945 A1 | * | 9/2004 | Heasley | ..................... 433/136 |

* cited by examiner

*Primary Examiner*—John J Wilson
(74) *Attorney, Agent, or Firm*—David George Johnson

(57) ABSTRACT

A rubber dam (1) used for protecting a patient (2) during dental procedures. The dam (1) includes a symmetrical round frame (3) which supports a flexible membrane (11). A prepunched hole (19) located approximately 0.5 inch from the membrane center (18) permits rotation of the frame (3) in order to position the hole (19) over the desired tooth (13) without causing the relative position of the frame (3) with respect to the patient's face to be substantially altered.

1 Claim, 3 Drawing Sheets

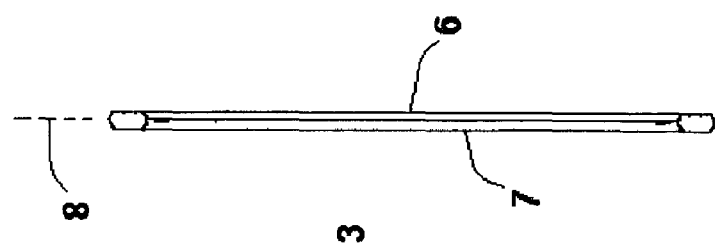
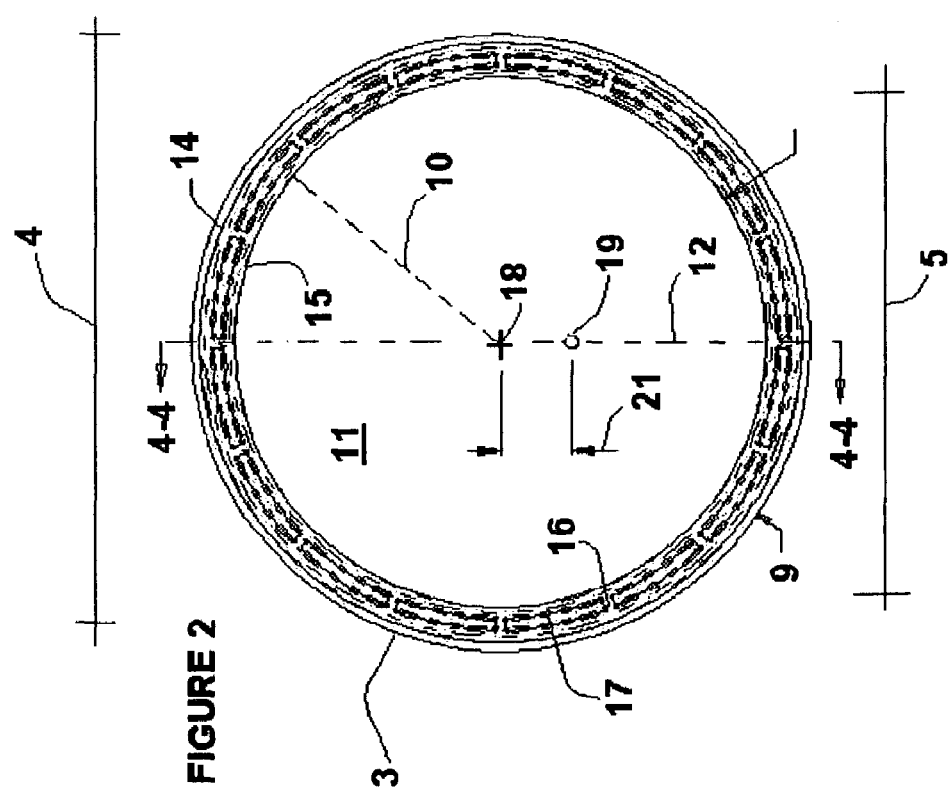

SYMMETRICAL RUBBER DAM HAVING A TOOTH GRIPPING ORIFICE

FIELD OF THE INVENTION

The present invention relates generally to the use of rubber dams used in performing dental procedures, and more particularly to a rubber dam construction which eases the task of positioning the dam over the patient's mouth and face by using a hand moldable frame that maintains structural integrity.

BACKGROUND OF THE INVENTION

As is well known the so called rubber dam technique is sometimes used in dental practice in certain procedures, particularly those in which a large number of small instruments, fittings, chemicals or debris are expected to be introduced into the patient's mouth during the procedure. This technique is the standard of care employed during root canal procedures in order to define a treatment area within the mouth which protects the patient and is not contaminated with saliva. A rubber dam is normally applied by punching a hole in the dam immediately prior to use and then slipping the punched hole over the tooth or teeth to be treated. The rubber dam is held in place by special clamps or ligatures.

The perimeter areas of the rubber dam are usually supplied with elastic retention devices that are placed around the ears or the back of the patient's head, often creating discomfort. Further, the act of securing the rubber frequently disturbs the proper positioning of the dam itself and necessitates placing additional holes in the dam membrane to gain access to the desired tooth. Since multiple perforations of the rubber dam tend to defeat its primary purpose as a barrier, the first rubber dam must be discarded and a second dam utilized. Many dentists forego the use of the rubber dam because its use, while very desirable in theory, is often just too bothersome and time consuming in practice.

Examples of previous rubber dams include the device described in U.S. Pat. No. 2,680,908, entitled DENTAL ISOLATOR AND CONE, issued to Daigle on Jun. 15, 1954, in which a frame and sheet is retained in the mouth by the biting action of opposed teeth. U.S. Pat. No. 3,772,790, entitled TOOTH ISOLATING SHIELD, issued to Swan-Gett on Nov. 20, 1973, discloses a tooth isolating shield having an apron of a deformable material and semirigid dentition bridge conforming members. The Swan-Gett device suffers from the common drawback of requiring that it be tailored to conform to the individual patient's mouth.

The use of an inflatable frame is disclosed in U.S. Pat. No. 3,781,994, entitled ARRANGEMENT FOR SEPARATING AN AREA OF OPERATION OR TREATMENT IN THE ORAL CAVITY, issued to Hesselgren on Jan. 1, 1974. The Hesselgren device utilizes a frame that must be inflated by compressed air in order to stretch the rubber dam into a bowl or funnel shape. U.S. Pat. No. 4,600,387, entitled RUBBER DAM FRAME FOR DENTAL WORK discloses a rubber dam in which a portion of the frame actually resides within the patient's oral cavity, causing substantial discomfort. Further, the resilient rubber sheet must be placed on frame by the dentist at the time of use. Finally, U.S. Pat. No. 4,828,491, entitled UNITARY PREASSEMBLED DISPOSABLE INTRA-ORAL RUBBER DAM DEVICE, issued to Gray on May 9, 1989, also discloses a rubber dam in which the frame is placed within the oral cavity and is retained in place by the force of its resilient frame pressing against the inside of the patient's mouth. The Gray device can potentially obstruct the patient's airway.

In summary, previous attempts to produce a practical rubber dam device have resulted in structures which are awkward to assemble and position as well as uncomfortable for the patient to endure during a lengthy procedure. In addition, the lack of compact dimensions fitting outside of the lips sometimes intimidates fearful patients. This can result in panic attacks and the false perception by the patient that their airway is obstructed. The result is that many dentists have abandoned their use despite the obvious safety advantages offered by rubber dam technology.

SUMMARY OF THE INVENTION

The present invention is an improved rubber dam that addresses many of the problems associated with prior art devices. In particular, the present invention includes a circular, octagonal or other similarly symmetrical frame to which is bonded a resilient, translucent or opaque rubber like material. The frame shape offers the advantage that rotation and repositioning of the frame by the dentist does not substantially change the orientation or footprint of the frame on the patient's face. Thus rotation of the frame does not result in a corner or edge of the frame suddenly pressing into the patient's eye, nose or cheek as is common in prior art rectangular, elliptical or asymmetrically shaped rubber dam devices. The shape of the frame of the present invention also permits the dam to be quite small (on the order of three to five inches) along its greatest dimension while still having a frame that resides completely outside of the patient's mouth, yet not in contact with the patient's eyelids, ears, nose, cheeks, chin or neck. The material of the frame, a high density polyethylene plastic, is repeatedly hand deformable to an infinite variety of positions. Unique to the present invention is the ability of the frame to maintain the newly created shape or position. Thus, the dentist may bend the frame to the desired shape to make a custom fit to the patient's face and may also fold the frame to permit taking an x-ray.

The flexible membrane material of the present invention is chosen to provide strength, deformability and translucence. The proper combination of those characteristics has eluded prior art researchers in this field and has complicated the dam positioning process. In particular, dam translucency is important in permitting placement of the dam accurately on the tooth without tearing the tooth admitting hole and without scraping or sliding the frame across the patient's face. The dentist can see the tooth through the membrane and immediately place the hole over the tooth without estimation or trial and error. The rubber like material is permanently bonded to the frame and does not require any assembly by the dentist at the time of use. This is a significant advantage since the material is most vulnerable to damage when subjected to a shearing force such as may be experienced when placing the material on the retaining spikes of a conventional frame by hand. Further, the membrane material is chosen to have a relaxed grip while maintaining its shape, unlike prior art membranes which are either completely rigid or stretched taut in order to provide the needed dam shape while maintaining their attachment to their frame.

The present invention also includes a prepunched off center orifice through which the tooth is placed. Prepunching was not possible in prior art devices because the lack of a symmetrical frame shape prevented prediction of the proper orifice position. Punching of the hole by the dentist at the time of use often resulted in a poorly shaped hole creating tearing of the dam membrane when stretched, and the inability to freely rotate the asymmetrically shaped dam frame often required punching multiple holes to finally achieve the desired location. The unique shape of the frame of the present invention permits the hole to be prepunched in a repeatable, controlled fashion in a factory environment. Typically the hole is placed approximately one half inch off center. Thus, by simply rotating the frame the position of the prepunched hole can be moved over the desired tooth without significantly changing the position of the frame on the patient's face. Once the desired location is achieved, traditional rubber dam tooth clamps, well known in the art, are used to secure the membrane to the tooth. The lightweight and small, symmetrical size of the present invention permits the use of only a tooth clamp to secure the dam during the dental procedure without the need for additional straps, lines, wedges or tape.

BRIEF DESCRIPTION OF THE DRAWINGS

FIG. 2 is a front elevation of a first embodiment of a rubber dam constructed according to the principles of the present invention;

FIG. 3 is a side elevation of a second embodiment of a rubber dam constructed according to the principles of the present invention.

DETAILED DESCRIPTION OF THE PREFERRED EMBODIMENTS

Figure 1:
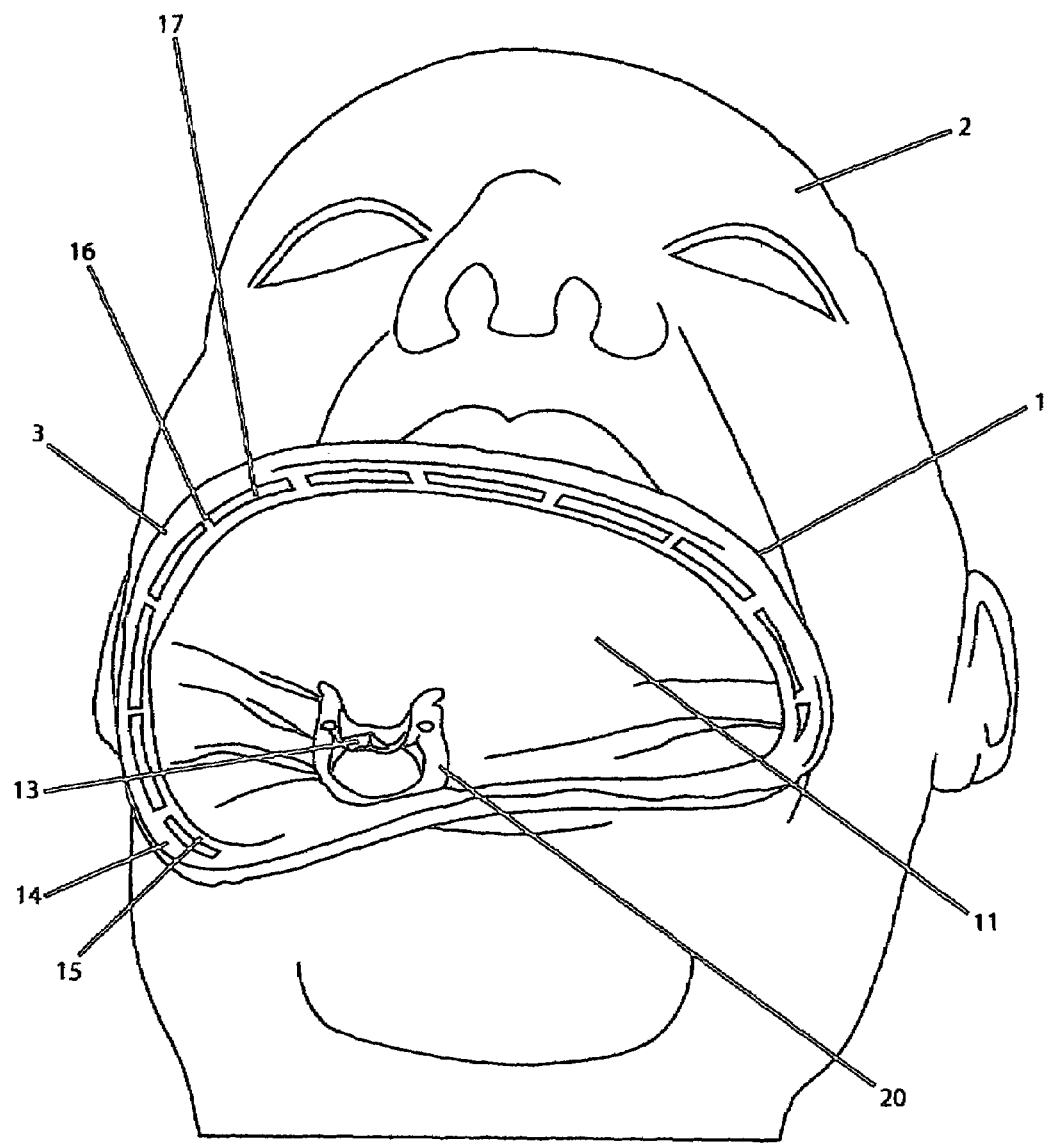
FIG. 1 is a pictorial view of a rubber dam constructed according to the principles of the present invention, shown while being used with a human patient.
Figure 4:
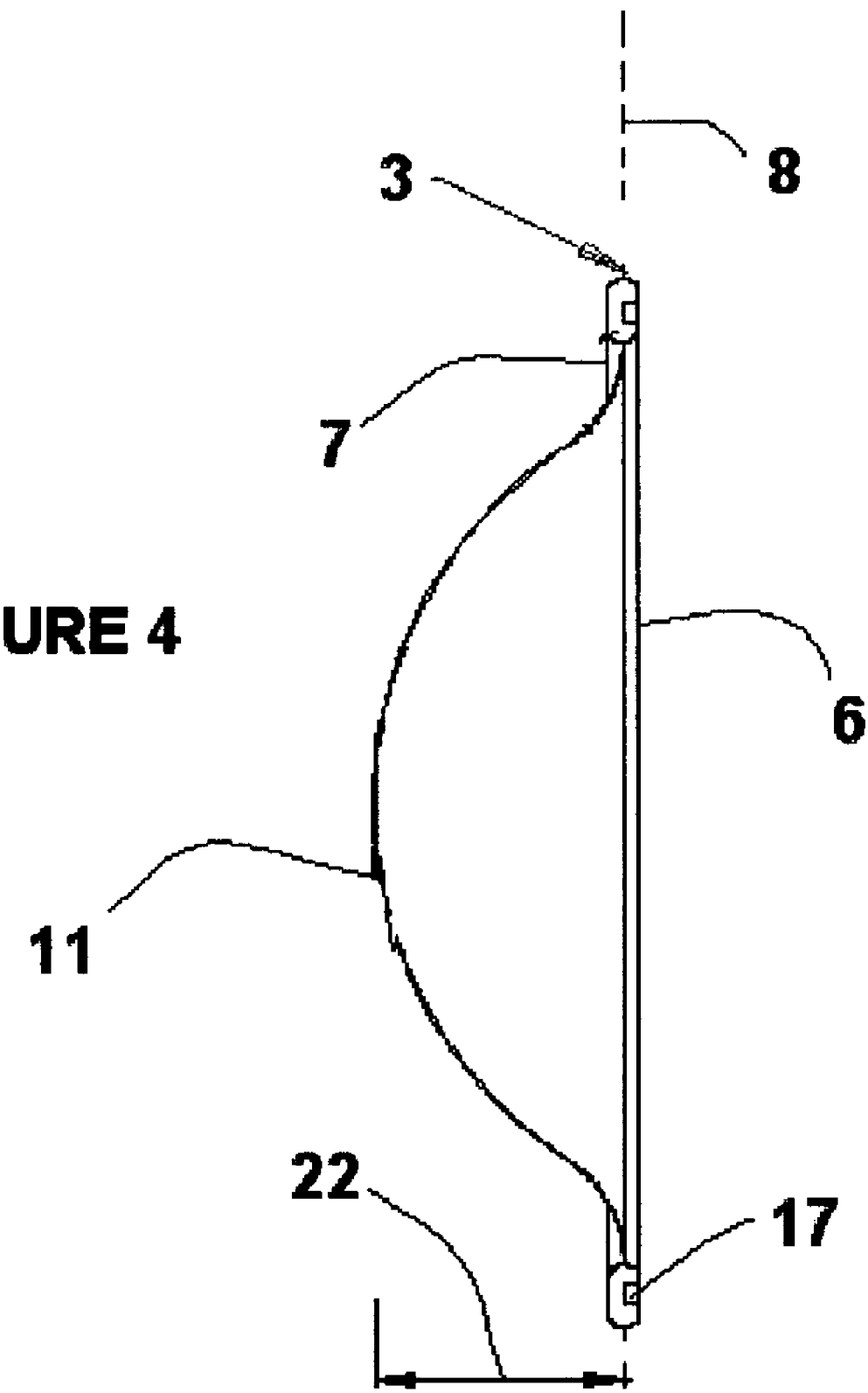
FIG. 4 is a sectional view taken along lines 4—4 of the rubber dam depicted in FIG. 2.

Referring to FIG. 1, a rubber dam constructed according to the principles of the present invention is shown generally at 1, while being worn by a patient 2. The dam 1 includes a flexible molded plastic frame 3. Referring also to FIG. 2, the dam 1 has nominal outside diameter 4 of 4.25 inches and a nominal inside diameter 5 of 3.75 inches. As best seen in FIG. 3, the plastic frame 3 is formed of a first half 6 and a substantially identical second half 7. The frame 3 is formed from a lightweight plastic such as high density polyethylene or any lightweight material with sufficient rigidity to support membrane 11 while permitting repeated bending and reshaping of frame 3 by hand. In particular, the frame may be folded, bent or curved from the plane 8 in which it resides, repeatedly, to conform to the particular requirements of the dental procedure being performed as well as the contours of the face of patient 2. When bent, the material of frame 3 permits the frame to assume the new shape and position until the dentist reshapes and rebends the frame 3 to assume a new configuration.

In FIGS. 1 through 4 the frame 3 is circular, but the frame 2 can be any substantially circular configuration such as an octagon, dodecagon or any other symmetrical configuration which lacks sharp corners or edges and does not have a longitudinal dimension that is substantially greater than its lateral dimension. An important requirement of the shape of frame 3 is that it allow a perimeter or sector region of the frame 3 to be folded over the remaining portion of the frame 3 without residing substantially outside of the original area or footprint of the frame 3. In other words, the frame 3 illustrated in FIG. 2 may be folded along diameter line 12, resulting in a smaller area that lies completely within the boundary or perimeter 9 of the unfolded frame 2. This would also be true if the frame 3 was folded along, for example, radial line 10. This foldability is a significant advantage of the present invention because it permits the dam 1 to be positioned on the desired tooth 13 and reduced in size by folding, if desired, with the certain knowledge that the frame 3 will occupy no new area of the face of the patient 2.

Each frame half 6, 7 is formed to have an outer rib 14 and an inner rib 15, the inner and outer ribs being joined by a series of radially extending spokes 16. The result of this construction is to create a series of lightening holes or voids 17 which result in a lower gross weight for the frame 3 and also increase its flexibility while maintaining the necessary stiffness to preserve the shape of frame 3.

Sandwiched between the frame halves 6 and 7 is membrane 11. Membrane 11 is formed of a natural latex material having a thickness of approximately 0.25 mm. This thickness insures the transparency necessary to permit viewing of the tooth during positioning of the frame 3 by the dentist. The tensile strength of the membrane 11 is approximately 4,000 psi (27 MPa) with an ultimate elongation before failure of approximately 800%. The tear strength is approximately 40 N/mm and the specific gravity is approximately 0.935. In the first embodiment shown in FIGS. 2 and 4, the membrane 11 is deformed so that its center 18 is displaced a distance 22 that is approximately one inch from the plane 8 of the frame 3, thereby assuming the shape of a bowl. The deformation of the membrane 11 is due entirely to the force of gravity displacing an excess amount of material gripped between the frame halves 6 and 7, and results in relatively less surface tension on the membrane 11 when placed on a patients tooth 13 that is located toward the rear of their mouth. In an alternate embodiment of the present invention, the membrane 11 is placed between the frame halves 6 and 7 in a flat, unstretched state. Thus the membrane 11 is in a planar but not taut configuration. Once in place the two frame halves 6 and 7 are fastened together by welding, an adhesive or any other suitable plastic bonding process. Once secured within the frame 3 the center 18 of membrane 11 may be readily displaced at least an inch without approaching the failure point of membrane 11.

Punched within the membrane 11 is orifice 19, having a diameter of approximately 0.093 inch. The orifice 19 is located a distance 21 of approximately 0.50 inch from the center 18 of the membrane 11. The diameter of orifice 19 is such that it is smaller that the lateral dimension of the typical tooth 13. The latex material of membrane 11 stretches around the tooth 13 and provides a modest gripping force. In use, a standard or winged clamp 20 is then used to secure the membrane 11 to the tooth 13. When a winged clamp 20 is used, the winged clamp may be placed into orifice 19 and then the winged clamp and orifice 19 may be simultaneously placed over the desired tooth 13. When using a standard clamp (not shown), the orifice 19 is first placed over the desired tooth 13 and then the standard clamp is placed on the tooth.

Although a specific design for the rubber dam of the present invention has been described, it will be apparent to those of skill in the art that other means of practicing the invention are possible without departing from the spirit and scope of the invention. For example the specific construction of the membrane retaining frame can vary widely as long as the membrane is adequately supported and the symmetry of the frame shape is maintained.

I claim:

1. A substantially circular rubber dental dam, comprising:
   (a) a high density polyethylene membrane;

(b) a resilient latex frame, the membrane being affixed to the frame, the frame being repeatedly deformable by hand manipulation to assume a desired shape, (c) a prepunched circular orifice, the prepunched circular orifice residing at a distance of approximately 0.5 inch from a membrane center, the prepunched circular orifice having a diameter of approximately 0.093 inch; and (d) a plane, the plane being defined by a diameter of the resilient latex frame, the membrane being affixed by an edge portion to the resilient latex frame, the membrane being dimensioned such that a central region of the membrane has a deformation residing outside of the plane, the deformation of the membrane being due entirely to a gravitational force displacing the central region of the membrane, thereby permitting the frame to rest upon a human face while the prepunched circular orifice surrounds a human tooth and the central region of the membrane extends into a human mouth while the membrane remains in a relatively untensioned state.

* * * * *